United States Patent [19]
Takahashi et al.

[11] Patent Number: 5,359,991
[45] Date of Patent: Nov. 1, 1994

[54] COVER DEVICE FOR ENDOSCOPE

[75] Inventors: Nagashige Takahashi; Teruo Ouchi; Hiromichi Shibuya, all of Tokyo, Japan

[73] Assignee: Asahi Kogaku Kogyo Kabushiki Kaisha, Tokyo, Japan

[21] Appl. No.: 871,711

[22] Filed: Apr. 21, 1992

[30] Foreign Application Priority Data

Apr. 24, 1991 [JP] Japan ................... 3-187112
May 31, 1991 [JP] Japan ................... 3-228165

[51] Int. Cl.⁵ ........................................... A61B 1/00
[52] U.S. Cl. ........................................ 128/4; 359/510
[58] Field of Search ................ 128/4, 6; 359/510

[56] References Cited

U.S. PATENT DOCUMENTS

| | | | |
|---|---|---|---|
| 3,528,720 | 9/1970 | Treale | 359/510 |
| 4,741,326 | 5/1988 | Sidall et al. | 128/4 |
| 4,825,850 | 5/1989 | Opie et al. | 128/4 |
| 4,852,551 | 8/1989 | Opie et al. | 128/4 |
| 4,907,395 | 3/1990 | Opie et al. | 53/434 |
| 4,944,287 | 7/1990 | Takahashi et al. | 128/4 |
| 4,991,564 | 2/1991 | Takahashi et al. | 128/4 |
| 4,991,565 | 2/1991 | Takahashi et al. | 128/4 |
| 5,005,755 | 4/1991 | Takahashi et al. | 228/126 |
| 5,007,406 | 4/1991 | Takahashi et al. | 128/4 |
| 5,050,585 | 9/1991 | Takahashi | 128/4 |
| 5,058,567 | 10/1991 | Takahashi et al. | 128/4 |
| 5,105,800 | 4/1992 | Takahashi et al. | 128/4 |
| 5,168,863 | 12/1992 | Kurtzer | 128/4 |
| 5,201,908 | 4/1993 | Tones | 128/4 |

*Primary Examiner*—Stephen R. Crow
*Assistant Examiner*—Beverly A. Meindl
*Attorney, Agent, or Firm*—Sandler, Greenblum & Bernstein

[57] ABSTRACT

A cover device which is removably fitted over an endoscope to cover an insert part of the endoscope and a control part connected to the proximal end of the insert part. The cover device includes a tubular sheath for covering the insert part so as to isolate it form the outside, and a control part cover for wrapping the control part. The control part cover is separate from the sheath and spreadably provided in contiguity with the proximal end of the sheath. In addition, a fluid supply tube is disposed such that one end portion of the tube extends through the sheath to communicate with the distal end of the sheath. The other end portion of the tube extends from the proximal end of the sheath along the outside of the control part cover.

14 Claims, 15 Drawing Sheets

COVER DEVICE FOR ENDOSCOPE

BACKGROUND OF THE INVENTION

The present disclosure relates to subject matter contained in Japanese Patent applications No. 3-187112 (filed on Apr. 24, 1991) and No. 3-228165 (filed on May 31, 1991), which are expressly incorporated herein by reference in their entireties.

1. Field of the Invention

The present invention relates to a cover device used for an endoscope to prevent the endoscope from coming into direct contact with the patient's body during inspection of a hollow organ of the body.

It is necessary to prevent the contagion of bacteria and viruses from one patient to another, or from a patient to a doctor through an endoscope. It has recently been proposed to fit a cover device over an endoscope so as to prevent the patient and the doctor from direct contact with the endoscope during endoscopic inspection (endoscopy), and to replace the cover device with a new one for each endoscopy.

2. Description of the Prior Art

Such a cover device for an endoscope needs a sheath for covering the insert part of the endoscope and a cover for wrapping the control part of the endoscope. In a conventional cover device, a cylindrical cover for the control part is secured to the proximal end of the sheath, so that the cover device has an integral structure as a whole.

To remove such a conventional cover device from the endoscope, after the completion of an endoscopy, the sheath and the control part cover cannot be removed separately. Accordingly, it has been conventional practice to first remove the control part cover from the control part and turn it over toward the sheath, and then pull the sheath off the insert part of the endoscope, together with the control part cover that is turned thereover.

However, it is not easy to smoothly turn over the control part cover fitted over the control part of the endoscope, so that filth, such as mucus or blood, which is attached to the outer surface of the control part cover, may be scattered contaminating the surroundings during the operation of turning over the cover.

When pulled off the insert part of the endoscope, the sheath is accompanied by the control part cover, which is relatively large in size and unstable in form. Therefore, the insert part of the endoscope and the surroundings may be contaminated during the removal of the sheath.

In addition, an endoscopy, that is conducted with the cover device fitted over the endoscope, also needs to spurt air and water from the distal end portion of the endoscope, and to eliminate mucus and blood from a hollow organ of the patient's body by suction in the same way as in the case of the ordinary endoscopy. Accordingly, tubes for air and water supply and suction are needed.

Hitherto, such tubes are passed through the sheath and the control part cover. The channels of the tubes are opened and closed by control valves provided in the control part.

To remove such a cover device from the endoscope after the completion of an endoscopy, the tubes are disconnected from the control part after the control part cover has been removed from the control part.

In consequence, the tubes must be disconnected from the control part with the contaminated hands (gloves) that have touched the control part cover contaminated during the use. Thus, the contaminated hands must touch the control part during the disconnection of the tubes, resulting in contamination of the control part.

SUMMARY OF THE INVENTION

An object of the present invention is to provide a cover device for an endoscope which has no likelihood of contamination of the endoscope and the surroundings when the cover device is removed from the endoscope, after the completion of an endoscopy.

Other objects and advantages of the present invention will become apparent from the following detailed description of illustrated embodiments of the invention.

According to the present invention, there is provided a cover device which is removably fitted over an endoscope to covering an insert part of the endoscope and a control part connected to the proximal end of the insert part. The cover device includes a tubular sheath for covering the insert part so as to isolate it from the outside; and a control part cover for wrapping the control part, the control part cover being separate from the sheath and spreadably provided in contiguity with the proximal end of the sheath.

In addition, there is provided a cover device which is removably fitted over an endoscope to covering an insert part of the endoscope and a control part connected to the proximal end of the insert part. The cover device includes a tubular sheath for covering the insert part so as to isolate it from the outside; a control part cover provided in contiguity with the proximal end of the sheath to wrap the control part; and a fluid supply tube disposed such that one end portion of the tube extends through the sheath to communicate with the distal end of the sheath. The other end portion of the tube extends from the proximal end of the sheath along the outside of the control part cover.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below in detail with reference to the accompanying drawings.

Figure 1:
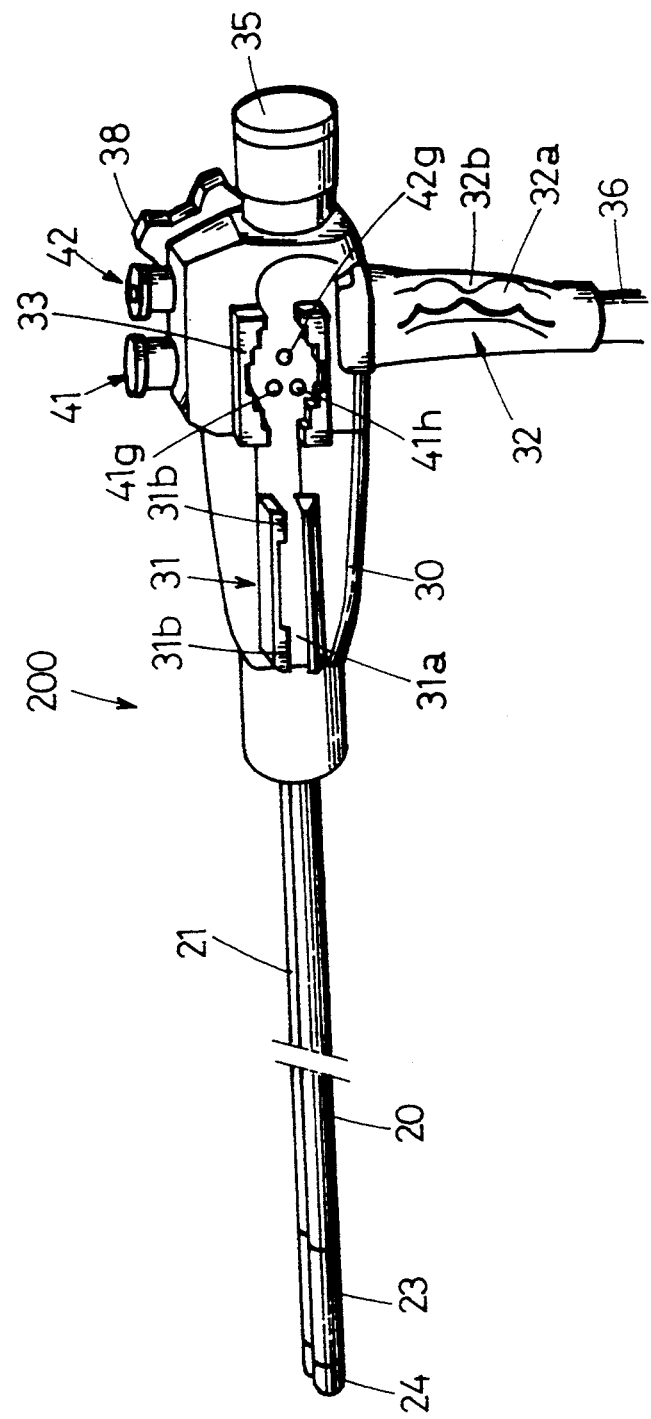
FIG. 1 is a perspective view of an endoscope in one embodiment of the present invention.

FIG. 1 shows an endoscope 200 that can be removably covered with the cover device of the present invention. The endoscope 200 has an insert part 20 formed from an elongate flexible tube. The top of the outer peripheral surface of the insert part 20 is formed with a U-shaped groove 21 extending axially over the entire length thereof.

A bendable portion 23, which is bendable by remote control, is formed at the distal end of the insert part 20. A distal end tip 24, that is provided with a pair of viewing and illuminating windows (not shown), is connected to the distal end of the bendable portion 23.

The endoscope 200 further has a control part 30 connected to the proximal end of the insert part 20. The control part 30 includes tube retainers 31 and 32 for securing fluid supply tubes of the cover device (described later) in position on the control part 30. Channel open-close controllers 41 and 42 are used to open and close channels formed by the fluid supply tubes. A socket 33 is adapted to secure the fluid supply tubes in a position opposite to movable pins 41g, 41h and 42g which are activated by the channel open-close controllers 41 and 42. These constituent elements will be described below one by one in detail.

An eyepiece 35 is used to observe an image sent from the viewing window through an image guide fiber bundle (not shown). A flexible tube 36 is connected to a light source apparatus (not shown) to send illuminating light from the light source apparatus to the illuminating window through a light guide fiber bundle inserted therein.

A bending control knob 38 is rotatably provided on the back of the control part 30 as viewed in FIG. 1, the knob 38 being detachable from the control part 30, as shown, for example, in Japanese Patent Application Laid-Open (KOKAI) No. 2-126825 (1990).

Figure 2:
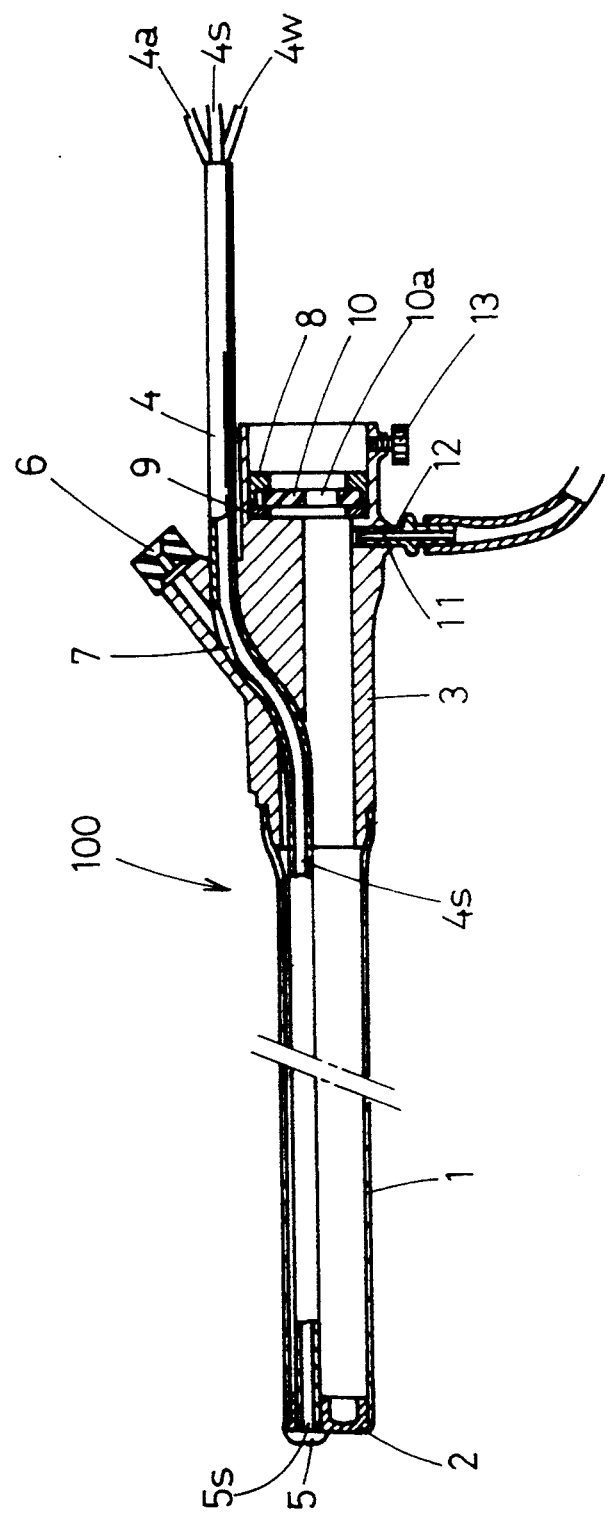
FIG. 2 is a sectional side view of a sheath in the embodiment of the present invention.
Figure 3:
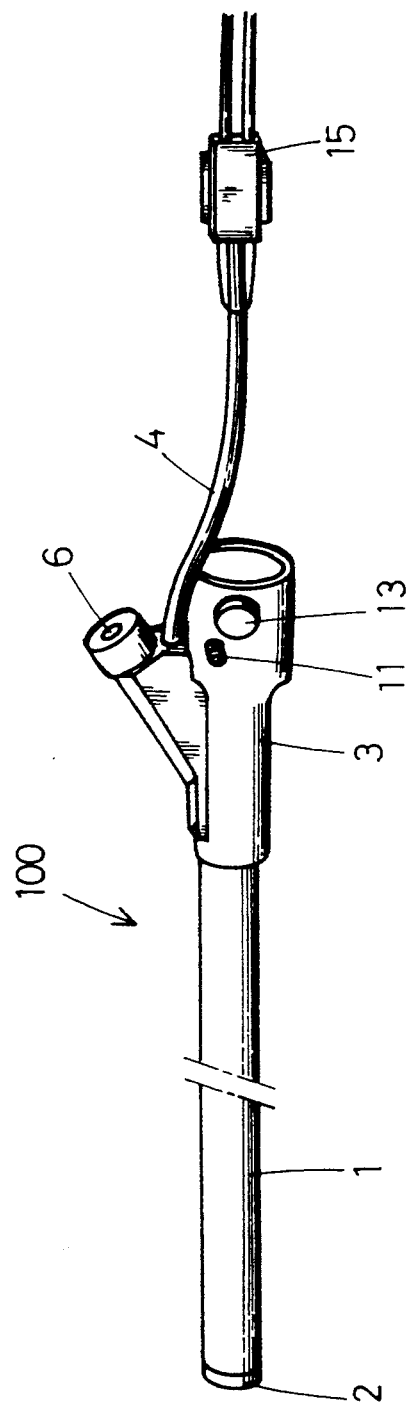
FIG. 3 is a perspective view of the sheath in the embodiment of the present invention.

FIGS. 2 and 3 show a tubular sheath 100 for covering the insert part 20 so as to isolate it from the outside, as a constituent element of the cover device according to the present invention. The sheath 100 comprises a tubular member 1, a distal end member 2 and a mouth member 3. The tubular member 1 is formed in the shape of a thin-walled cylinder that extends over substantially the entire length of the sheath 100, by using a stretchable and flexible material, for example, silicone rubber. The distal end member 2 is connected to the distal end of the tubular member 1 in such a manner that no gas will leak out of the sheath 100, the distal end member 2 being formed from a transparent material, e.g., a transparent styrol resin material. The rear end portion of the tubular member 1 is firmly bonded to the distal end portion of the mouth member 3, thereby connecting the tubular member 1 and the mouth member 3 in such a manner that no gas will leak out of the sheath 100.

A fluid supply tube 4, which is formed from, for example, tetrafluoroethylene resin, extends through the sheath 100 over the entire length thereof. The fluid supply tube 4 includes a suction tube 4s also serving as a forceps channel, an air supply tube 4a, and a water supply tube 4w. The fluid supply tube 4 is disposed along the groove 21 provided in the outer peripheral surface of the insert part 20. The rear end portion of the fluid supply tube 4 extends rearwardly from the mouth member 3, with the tubes 4s, 4a and 4w remaining in the integrated state over a certain length.

The distal end member 2 is formed with such an internal dimension that the distal end tip 24 of the endoscope is mildly fitted therein. A nozzle piece 5 projects from the end face of the distal end member 2. The nozzle piece 5 is provided with an air nozzle and a water nozzle, which face the viewing window when the distal end tip 24 is inserted into the distal end member 2.

The distal end member 2 is further provided with a suction opening 5s, also serving as a forceps opening, which opens forwardly. The suction tube 4s, the air supply tube 4a and the water supply tube 4w communicate with the suction opening 5s, the air nozzle and the water nozzle, respectively.

Reference numeral 6 denotes a forceps inlet which is provided in the mouth member 3. The side wall of the fluid supply tube 4 is provided with a bore 7 that provides communication between the suction tube 4s and the forceps inlet 6.

A packing 10, which is formed from an elastic material, is disposed near the mouth of the mouth member 3, with the packing 10 being sandwiched between metal frames 8 and 9. The packing 10 has a bore 10a which has a slightly smaller cross-sectional size than that of the insert part 20 of the endoscope, so that the packing 10 can hermetically seal the outer periphery of the insert part 20, without any gap. The insert part 20 can be smoothly inserted into and removed from the packing 10 without being caught therein.

An air supply opening 11 is provided in the mouth member 3 so as to be communicate with the tubular member 1. An air supply nipple 12 can be inserted into the air supply opening 11 to sending air into the sheath 100 so as to inflate the tubular member 1 when the insert part 20 of the endoscope is inserted into and removed from the sheath 100. Reference numeral 13 denotes a screw that is used to secure the mouth member 3 to the control part 30 of the endoscope.

Figure 4:
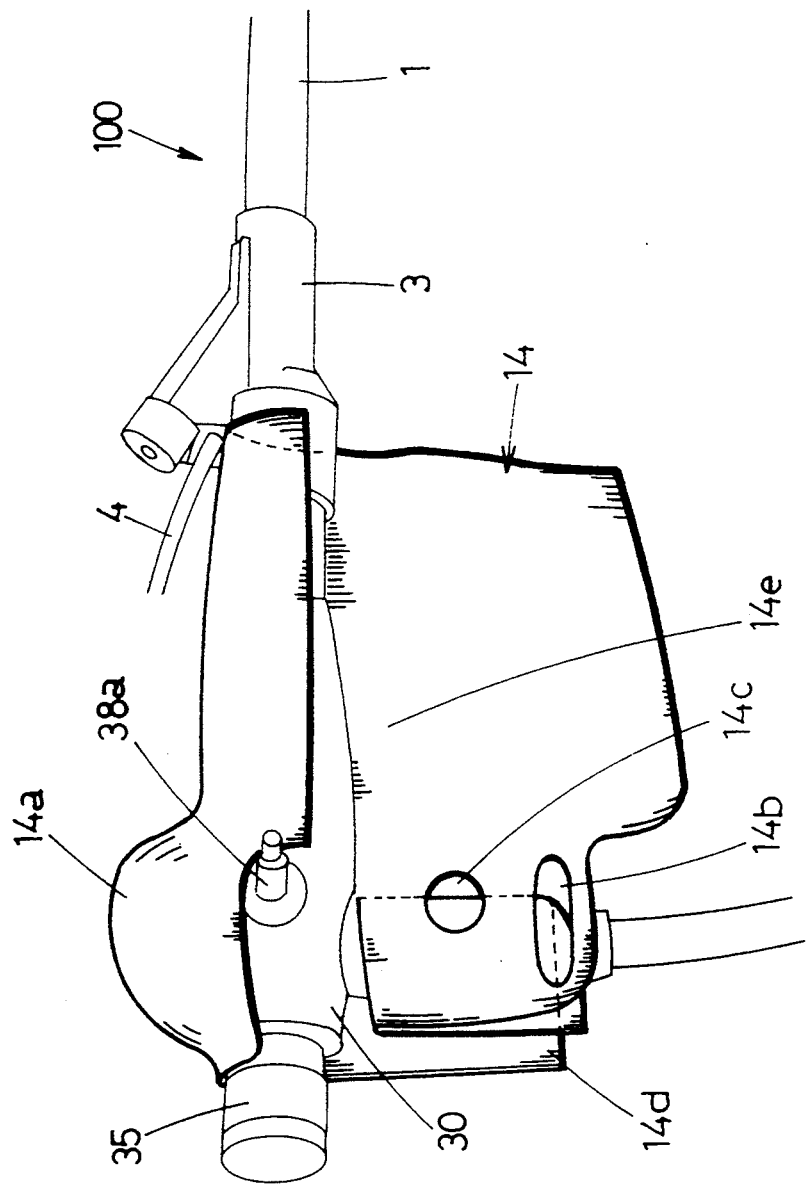
FIGS. 4 and 5 are perspective views of a control part cover in the embodiment of the present invention which is being attached to a control part of the endoscope.

FIG. 4 shows a control part cover 14 for wrapping the whole control part 30 of the endoscope. For facilitating the understanding of the arrangement, FIG. 4 shows the endoscope as viewed from the reverse side thereof, in contrast to the drawings described above, with the bending control knob 38 detached from the control part 30.

The control part cover 14 is formed from a single piece of flexible sheet material, for example, a non-rigid polyvinyl chloride sheet with a thickness of 0.05 mm to 0.5 mm, which is separate from the sheath 100 and spreadable independently of it. Either a transparent or semitransparent material is employed for the control part cover 14.

With one end portion of the control part cover 14 wound around the proximal portion of the eyepiece 35, the cover 14 wraps the control part 30 over the entire length thereof. However, in the case of a video endoscope, which has no eyepiece, the control part 30 is completely covered with the control part cover 14.

The other end portion of the control part cover 14 is wound around the outer periphery of the mouth member 3 of the cover device. The air supply opening 11 is covered with the control part cover 14. Accordingly, the air supply opening 11 is not contaminated during an endoscopy. The insert part 20 wrapped in the sheath 100 is not contaminated when air is supplied into the sheath 100 from the air supply opening 11, after the completion of an endoscopy.

The control part cover 14 protrudes outwardly in the form of a bag, at a portion (bag portion 14a) thereof, which covers a projection formed by the projecting portions of the channel open-close controllers 41 and 42, so that the control part cover 14 can be wound around the control part 30 as tightly as possible. Accordingly, the bag portion 14a is first put on and engaged with the projection of the control part 30. In this state, the wrapping portion 14e of the control part cover 14 is wrapped around the outer surface of the control part 30.

In addition, an engagement hole 14b is provided in the wrapping portion 14e of the control part cover 14 at the side thereof, which is remote from the bag portion 14a, such that the engagement hole 14b can be engaged with the projection of the control part 30 over the bag portion 14a put on the projection.

In addition, the control part cover 14 is provided with a hole 14c for passing a bending control shaft 38a, projecting from the control part 30. A portion of the control part cover 14, that covers the proximal portion of the flexible tube 36 for connection with the light source apparatus, is formed in a U-shape so that the proximal portion of the flexible tube 36 can be wrapped in the U-shaped portion 14d.

As shown in FIG. 4, the control part cover 14 is wrapped around the control part 30 solely after the insert part 20 of the endoscope has been completely inserted into the sheath 100.

Figure 5:
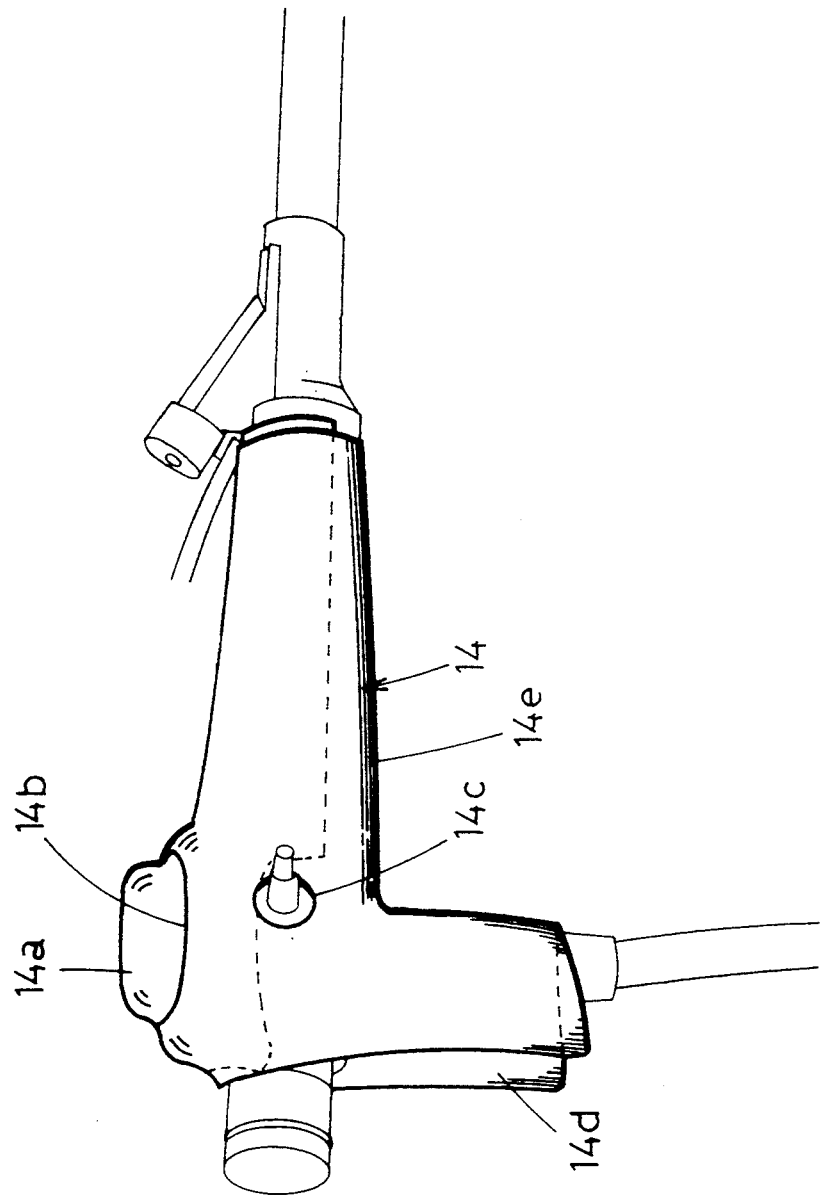

FIG. 5 shows the control part cover 14 in a state where the engagement hole 14b is engaged with the projection of the channel open-close controllers 41 and 42, over the bag portion 14a after the wrapping portion 14e has been wrapped around the outer surface of the control part 30. Thus the bag portion 14a is to be pressed against the projection of the channel open-close controllers 41 and 42 and thus tightly secured. In this way, the wrapping starting and terminating portions of the control part cover 14 are tightly engaged with the control part 30. Then, the U-shaped portion 14d is wrapped around the proximal portion of the flexible tube 36, in the state, as shown in FIG. 5, thus completing the wrapping of the control part 30.

Figure 6:
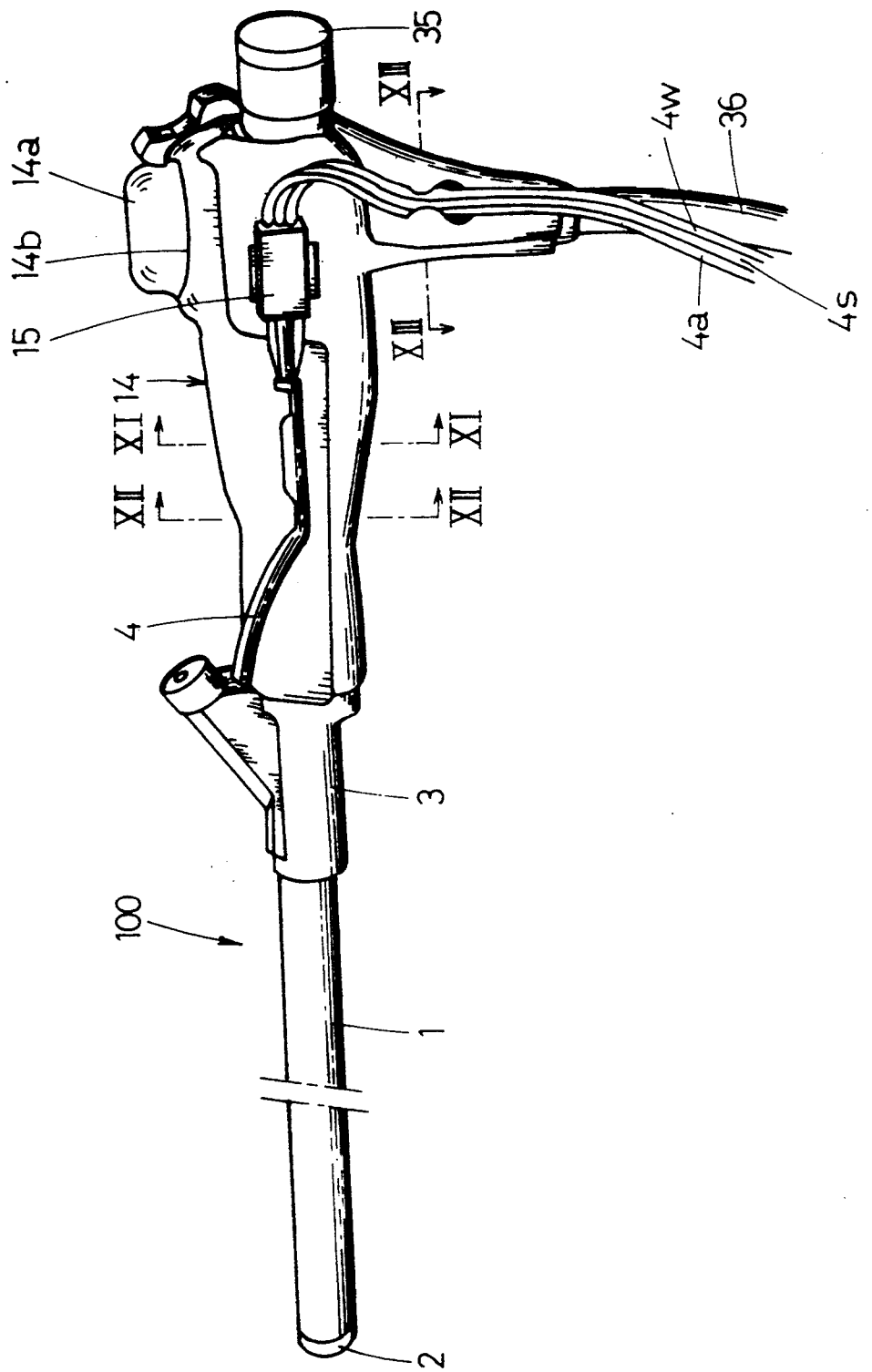
FIG. 6 is a perspective view of the embodiment of the present invention.

FIG. 6 shows the cover device which has been completely attached to the endoscope 200.

Figure 7:
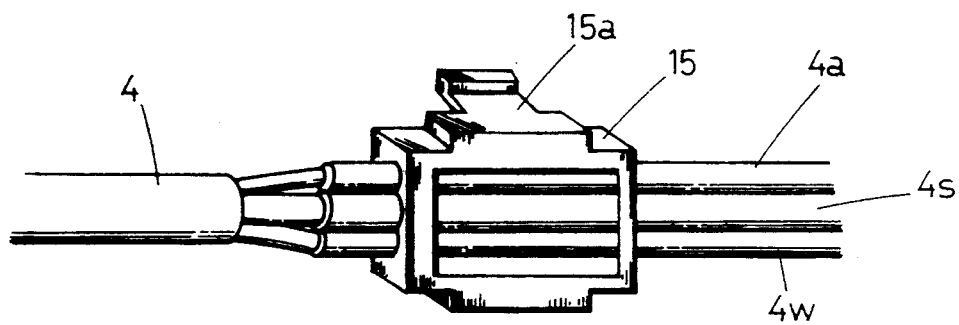
FIG. 7 is a perspective view of a tube support frame in the embodiment of the present invention.

The fluid supply tube 4, that extends from the mouth member 3 of the sheath 100, is led along the outside of the control part cover 14 and branches into three tubes 4s, 4a and 4w in the middle of the control part 30. As shown in FIG. 7, a tube support frame 15 is attached to the three tubes 4s, 4a and 4w to secure them in parallel with a short span.

Referring to FIG. 7, which shows the tube support frame 15 as viewed from the direction of the control part 30, the tubes 4s, 4a and 4w are fixed by both ends of the tube support frame 15, but the portions of the tubes 4s, 4a and 4w, which are intermediate between the two ends of the tube support frame 15, extend in parallel without being fixed. The tube support frame 15 has a pair of resilient engagement members 15a, for detachably engaging the tube support frame 15 with the socket 33 of the control part 30.

Figure 8:
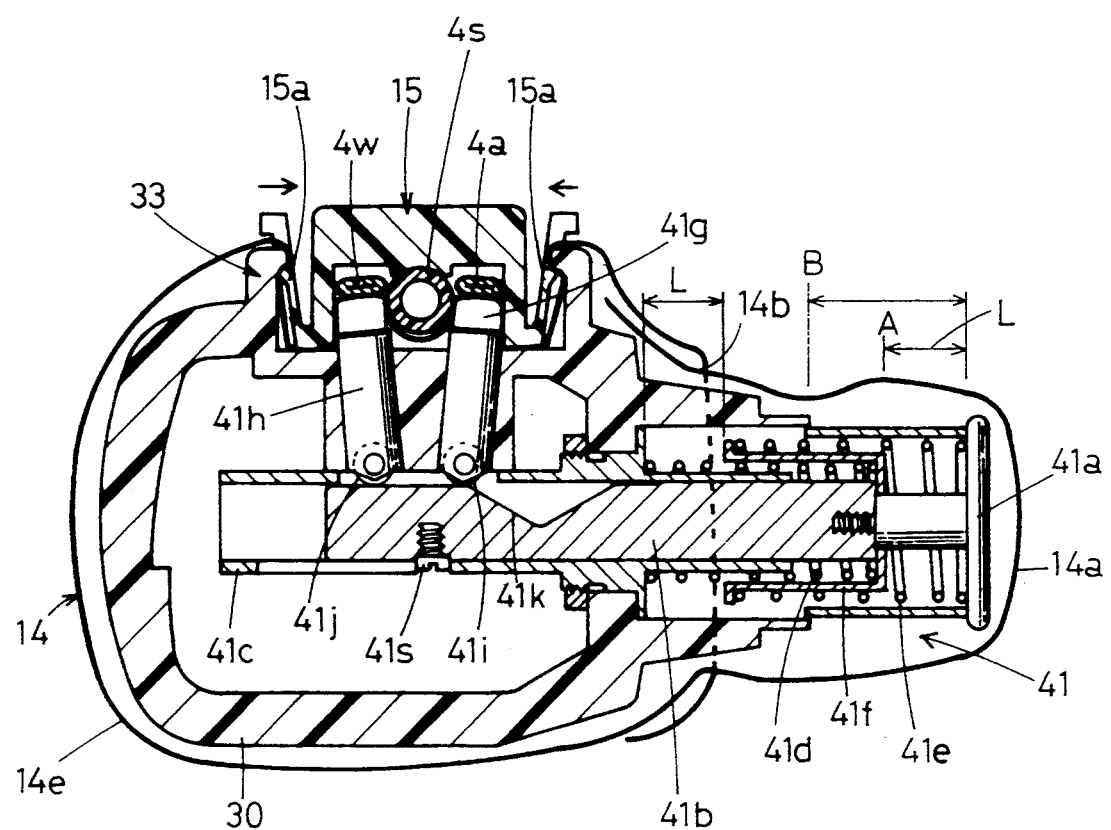
FIG. 8 is a sectional view of a channel open-close controller in the embodiment of the present invention.

FIG. 8 is a sectional view of the fluid supply controller 41 as a one channel open-close controller, which shows a state where the tube support frame 15 is attached to the socket 33.

As will be clear from FIG. 8, the engagement members 15a are engaged with the respective reverse sides of two projecting ends of the socket 33, thereby securing the tube support frame 15 to the socket 33.

Since the engagement members 15a are elastically deformable inwardly (in the directions of the arrows), the tube support frame 15 can be fixed in the state shown in FIG. 8, simply by pushing it into the socket 33. The tube support frame 15 can be removed from the socket 33 by elastically deforming the engagement members 15a inwardly (in the arrow directions) with fingers.

The control part cover 14 has no bore at a portion which faces the tube support frame 15, so that the cover 14 is sandwiched between the tube support frame 15 and the socket 33 at this portion and thereby secured to the control part 30. The air supply tube 4a and the water supply tube 4w are crushed by the movable pins 41g and 41h, respectively, with the control part cover 14 put therebetween.

As shown in FIG. 8, a piston 41b, that is connected directly to a fluid supply control button 41a, is movably provided in a cylinder 41c secured to the control part 30. A stopper 41s limits the stroke of the piston 41b.

The piston 41b is constantly biased outwardly by a first coil spring 41d and a second coil spring 41e which has a stronger spring force than that of the first coil spring 41d. An intermediate spring retainer 41f is provided between the two springs 41d and 41e so as to retain one end of each of the springs 41d and 41e.

Figure 9:
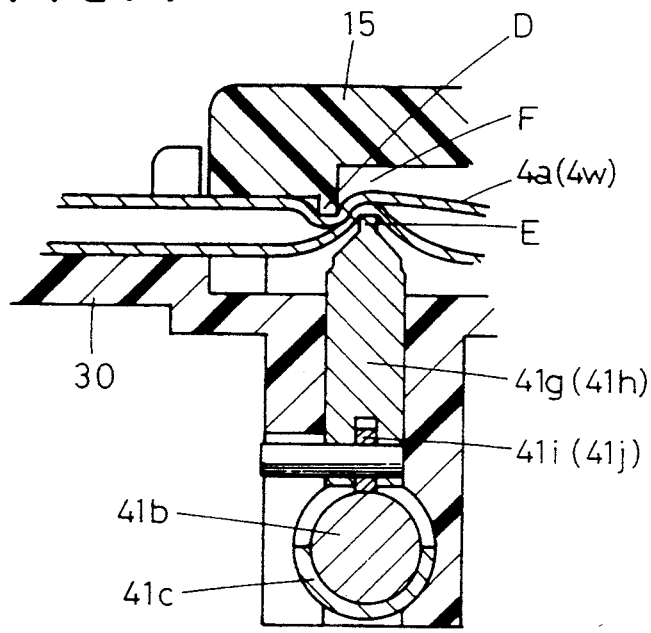
FIG. 9 is a fragmentary sectional view of the channel open-close controller in the embodiment of the present invention.

As shown in FIG. 9, a pair of movable pins 41g and 41h are movably disposed at one side of the piston 41b such that the outer ends of the pins 41g and 41h face the air and water supply tubes 4a and 4w, respectively. The movable pins 41g and 41h have respective rollers 41i and 41j, which are rotatably attached thereto and which are in contact with the side surface of the piston 41b. Normally (i.e., in a stand-by state), both the air and water supply tubes 4a and 4w are crushed by the respective movable pins 41g and 41h to close the channels.

FIG. 9 is an enlarged view of the crushed tube 4a (4w) seen from a different direction. A pair of tube pressing portions D and E, that press the tube 4a (4w), are respectively provided on the tube support frame 15 and the top of the movable pin 41g (41h), such that the pressing portions D and E project counter and parallel to each other with a little spacing provided therebetween. A clearance F is formed at the back of the tube 4a (4w) in front of the movable pin 41g (41h).

Accordingly, the tube 4a (4w) is deformed to a substantial degree by being pressed by the movable pin 41g (41h), so that the bore in the tube 4a (4w) is completely closed between the tube pressing portions D and E.

In addition, a relatively large V-shaped recess 41k is formed in the intermediate portion of the piston 41b, as shown in FIG. 8. Accordingly, when the fluid supply control button 41a is depressed as far as a halfway position A (stroke L) against the biasing force from the first coil spring 41d, the bottom of the recess 41k reaches the position of the movable pin 41g for air supply, so that the roller 41i at the lower end of the movable pin 41g is caused to move along the recess 41k by the restoring force of the air supply tube 4a, thereby opening the channel of the air supply tube 4a. Thus, air is suppied to the distal end of the sheath 100.

When the fluid supply control button 41a is further depressed, with a stronger force, as far as an inner position B against the biasing force from the second coil spring 41e, the bottom of the recess 41k of the piston 41b reaches the position of the movable pin 41h for water supply, so that the water supply tube 4w opens. Thus, water is supplied to the distal end of the sheath 100. At this time, the movable pin 41g, for air supply, is pushed up by the slope of the recess 41k, causing the air supply tube 4a to be closed again.

Figure 10:
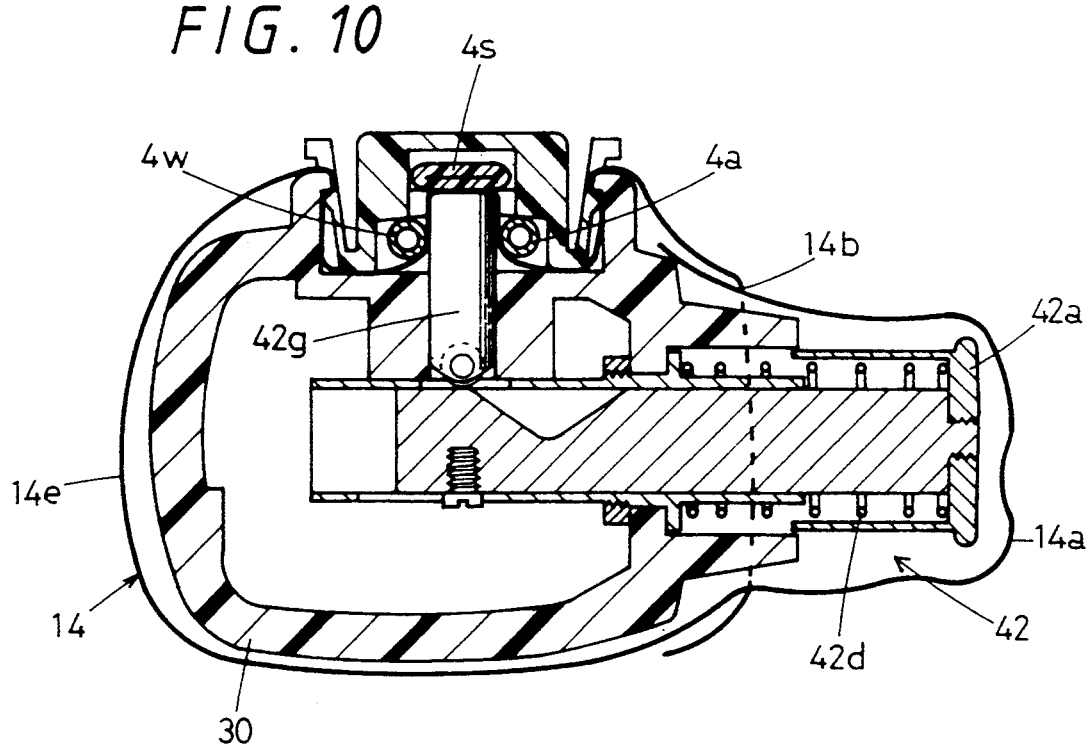
FIG. 10 is a sectional view of another channel open-close controller in the embodiment of the present invention.

FIG. 10 shows the suction controller 42 as another channel open-close controller. The suction controller 42 has the same arrangement as that of the fluid supply controller 41, except that the suction controller 42 is provided with only one movable pin 42g and only one coil spring 42d, because there is only one tube 4s to be controlled. Therefore, detailed description of the suction controller 42 is omitted. With the suction controller 42, when a suction control button 42a is depressed, suction is effected from the distal end of the sheath 100 through the suction tube 4s.

Figure 11:
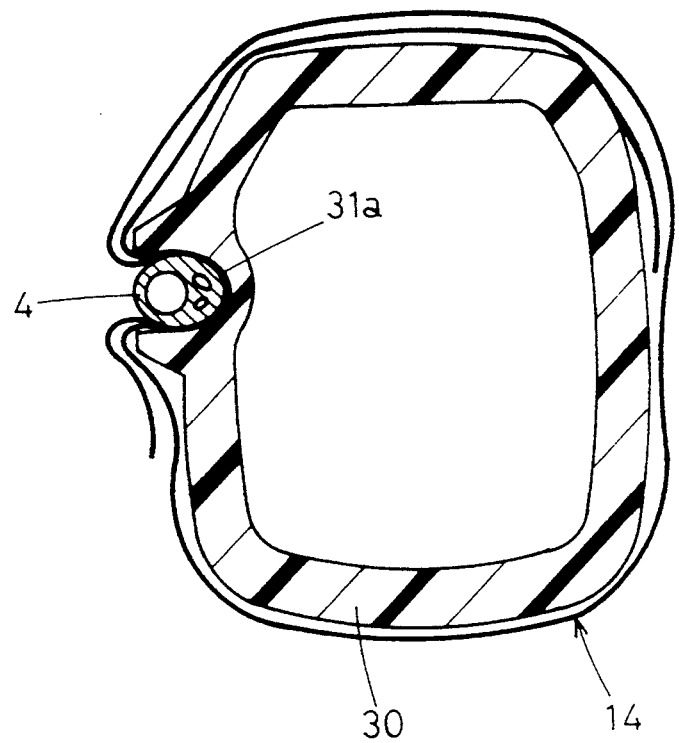
FIG. 11 is a sectional view taken along the line XI—XI in FIG. 6.
Figure 12:
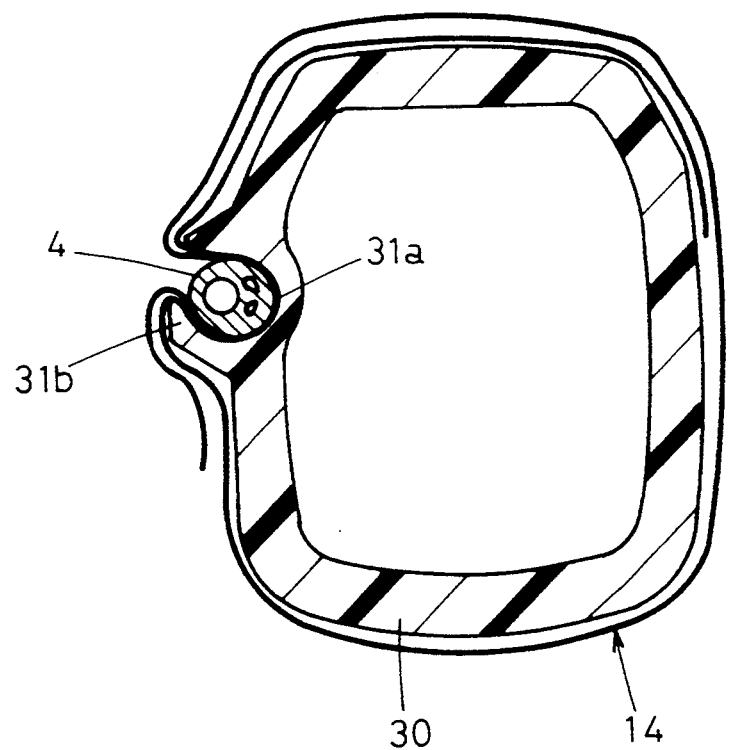
FIG. 12 is a sectional view taken along the line XII—XII in FIG. 6.

FIGS. 11 and 12 are sectional views taken along the lines XI—XI and XII—XII, respectively, in FIG. 6. At the illustrated portion of the control part 30, that is, the grip portion thereof, the air supply tube 4a, the water supply tube 4w and the suction tube 4s are formed in an integral structure as a single tube 4, which is fitted in a guide groove 31a with the control part cover 14 sandwiched therebetween. The guide groove 31a is defined between a pair of projecting portions of the surface of the plastics body of the control part 30.

Retaining portions 31b are respectively formed at both ends of the guide groove 31a to retain the fitted tube 4 from the outside, as shown in FIG. 12. Thus, the tube 4 is secured to the control part 30 with the control part cover 14 sandwiched therebetween by the retaining portions 31b so that the tube 4 will not disengage from the guide groove 31a. In other words, at the grip portion the control part cover 14 is tightly secured to the control part 30 by the tube 4. Accordingly, the structure is simplified, and the operation of attaching and removing the cover 14 is facilitated.

The tube 4 can be attached to and removed from the grip portion simply by slight elastic deformation of the tube 4.

Figure 13:
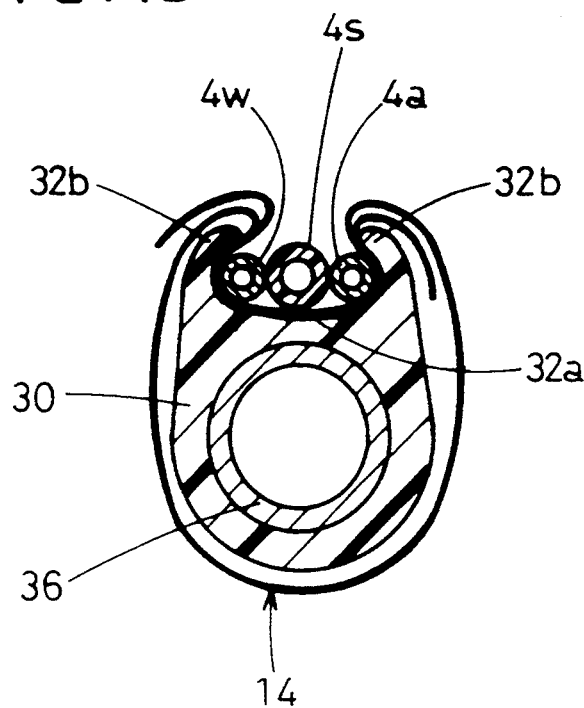
FIG. 13 is a sectional view taken along the line XIII—XIII in FIG. 6.

FIG. 13 is a sectional view taken along the line XIII—XIII in FIG. 6. At the proximal portion of the flexible tube 36, for connection with the light source apparatus, the control part 30 is formed with a guide groove 32a for fitting the three tubes 4s, 4a and 4w side by side. A pair of retaining portions 32b are respectively provided at both sides of the center of the guide groove 32a.

Thus, the three tubes 4s, 4a and 4w are secured to the control part 30 with the control part cover 14 sandwiched therebetween by the retaining portions 32b, so that the tubes 4s, 4a and 4w will not disengage from the guide groove 32a. In other words, at this portion, the control part cover 14 is also tightly secured to the control part 30 by the tubes 4s, 4a and 4w.

According to the embodiment arranged as described above, when the cover device is to be attached to the endoscope, first, air is supplied into the sheath 100 from the air supply opening 11 to inflate the tubular member 1 of the sheath 100. Then, the insert part 20 of the endoscope is inserted into the sheath 100, and the sheath 100 is locked in this state by the securing screw 13. Then, the control part 30 is wrapped with the control part cover 14 by executing the procedure shown in FIGS. 1, 5 and 6. The tube support frame 15 is attached to the socket 33. In addition, the tube 4 and the tubes 4s, 4a and 4w are fitted into the guide grooves 31a and 32a, thereby securing the control part cover 14 to the control part 30. Finally, the bending control knob 38 is attached.

Thus, the tubes 4, 4s, 4a and 4w are tightly secured to the control part 30 in a state where these tubes are disposed along the outside of the control part cover 14, so that air supply, water supply and suction can be controlled with the channel open-close controllers 41 and 42.

After the completion of an endoscopy, the cover device is removed from the endoscope by executing the procedure reverse to the above. More specifically, after the bending control knob 38 has been removed, the tubes 4, 4s, 4a and 4w and the tube support frame 15 are removed from the control part 30, and thereafter the control part cover 14 is removed from the control part 30.

Accordingly, there are no tubes or other elements to be removed from the control part 30 after the control part cover 14 has been removed from the control part 30. There is therefore no possibility of the control part 30 being contaminated.

In addition, the control part cover 14 can be removed from the control part 30 simply by removing the tubes 4, 4s, 4a and 4w without the need for removing other particular securing members or the like. Therefore, the operation is simple, and there is little likelihood of contamination of the surroundings.

In the state where the control part cover 14 has been removed from the control part 30, the sheath 100 is still attached to the insert part 20 of the endoscope. Accordingly, after the control part cover 14 has been completely removed, the sheath 100 is removed from the insert part 20 independently of the control part cover 14. It should be noted that the operation of fitting the sheath 100 over the insert part 20, or removing the former from the latter is conducted by inflating the tubular member 1 of the sheath 100 by use of a sheath cover disclosed, for example, in U.S. Pat. No. 4,991,564, after untightening the securing screw 13 to unlock the sheath 100.

Figure 14:
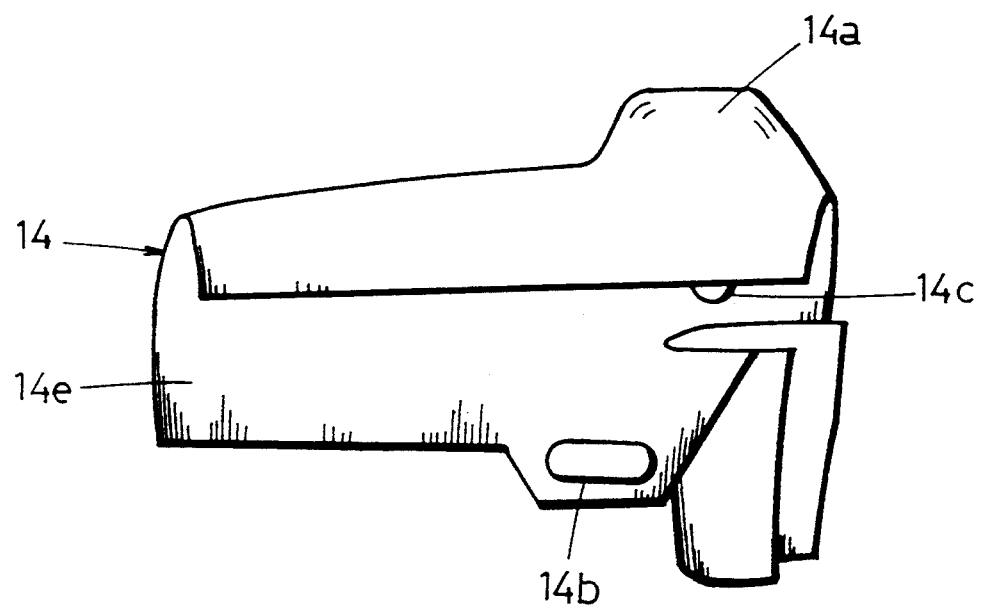
FIG. 14 is a perspective view of a control part cover in another embodiment of the present invention.

It should be noted that the present invention is not necessarily limited to the foregoing embodiment. For example, the bag portion 14a and the engagement hole 14b may be formed at respective positions reverse to those in the embodiment, as shown in FIG. 14. In this case, the engagement hole 14b is first engaged with the projection of the control part 30 of the endoscope. The bag portion 14a is put on the projection over the engagement hole 14b.

Figure 15:
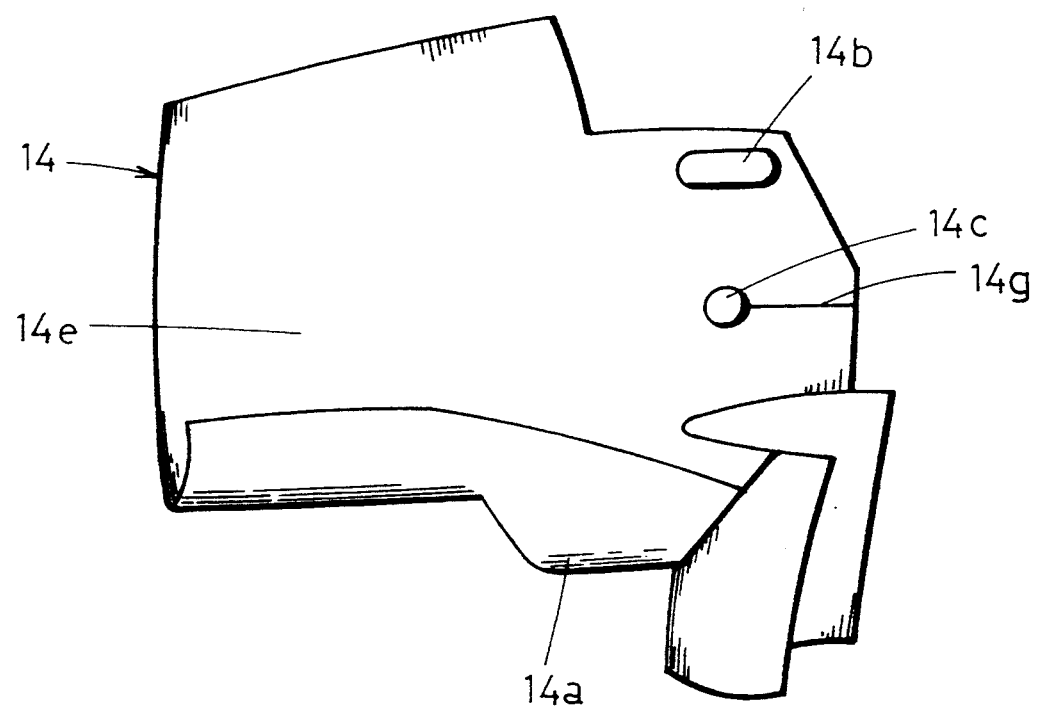
FIG. 15 is a perspective view of a control part cover in still another embodiment of the present invention.
Figure 16:
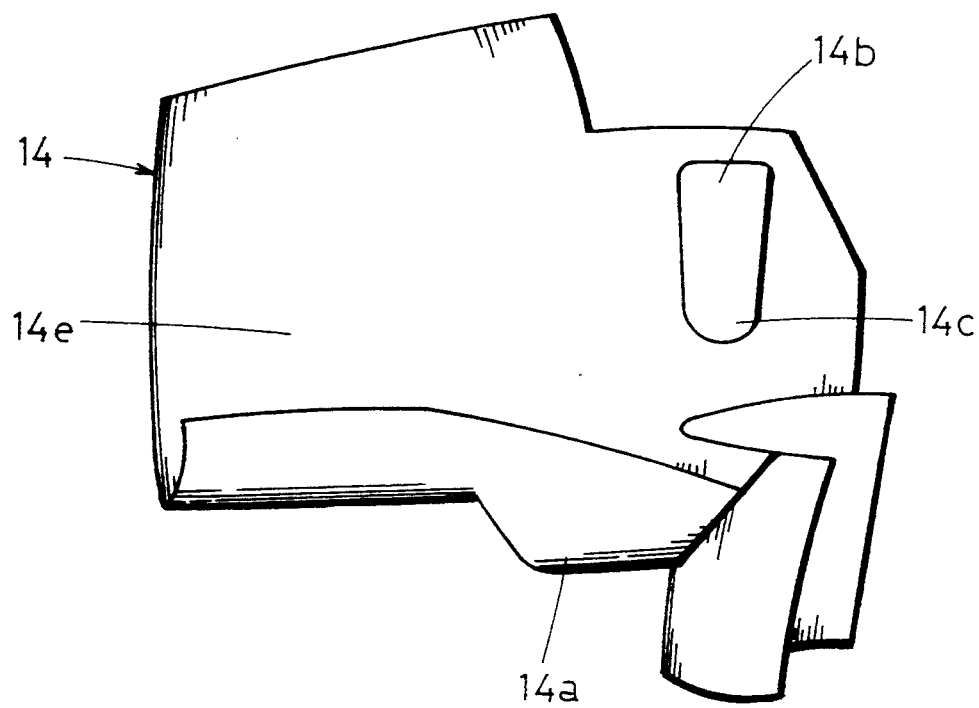
FIG. 16 is a perspective view of a control part cover in a further embodiment of the present invention.

The arrangement may also be such that the control part cover 14 is provided with a cut 14g that extends from the hole 14c to the outer edge of the control part cover 14 with a view enabling the bending control shaft 38a to be readily passed through the hole 14c, as shown in FIG. 15. Alternatively, the engagement hole 14b is enlarged so as to be continuous with the hole 14c for passing the bending control shaft 38a, as shown in FIG. 16.

Figure 17:
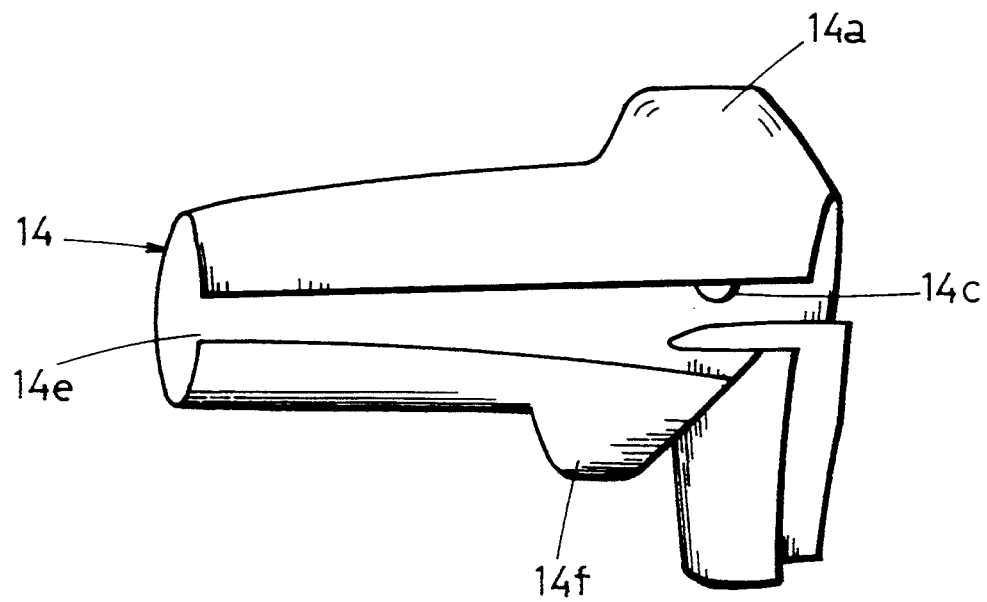
FIG. 17 is a perspective view of a control part cover in a still further embodiment of the present invention.

It is also possible to replace the engagement hole 14b, in the control part cover 14 with a second bag portion 14f, as shown in FIG. 17. In this case, the second bag portion 14f is put on and engaged with the projection of the control part 30 over the bag portion 14a, which is similarly put on and engaged with the projection, whereby the wrapping starting and terminating portions of the control part cover 14 are tightly engaged with the control part 30.

Figure 18:
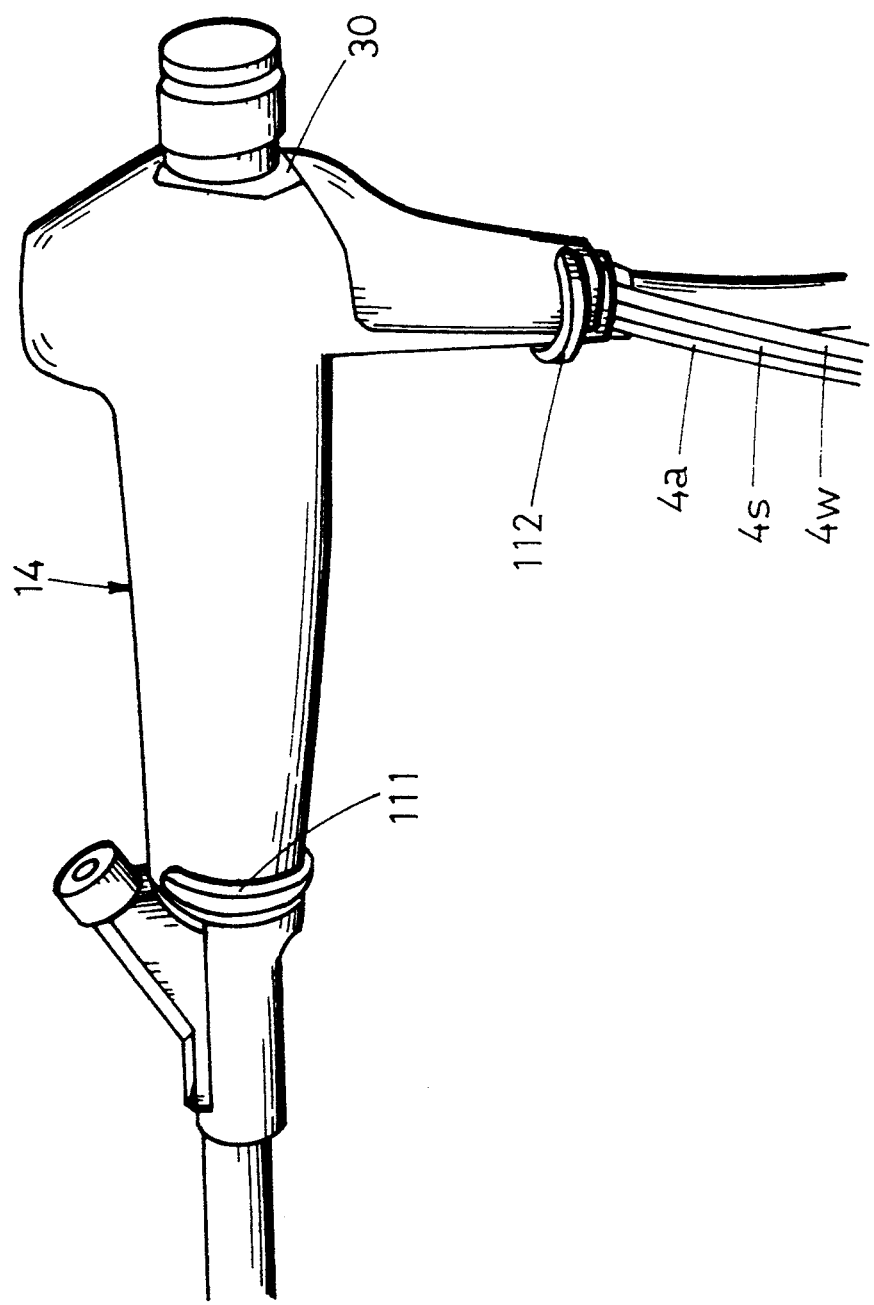
FIG. 18 is a perspective view of a control part cover in a still further embodiment of the present invention.

In a case where the tubes 4, 4s, 4a and 4w are passed through the inside of the control part cover 14, the control part cover 14 may be resiliently pressed against the control part 30 from the outside by using C-shaped retaining rings 111 and 112 made of a resilient plastic material, as shown in FIG. 18. The retaining rings 111 and 112 are removably attached to the control part 30 by deforming them elastically.

Figure 19:
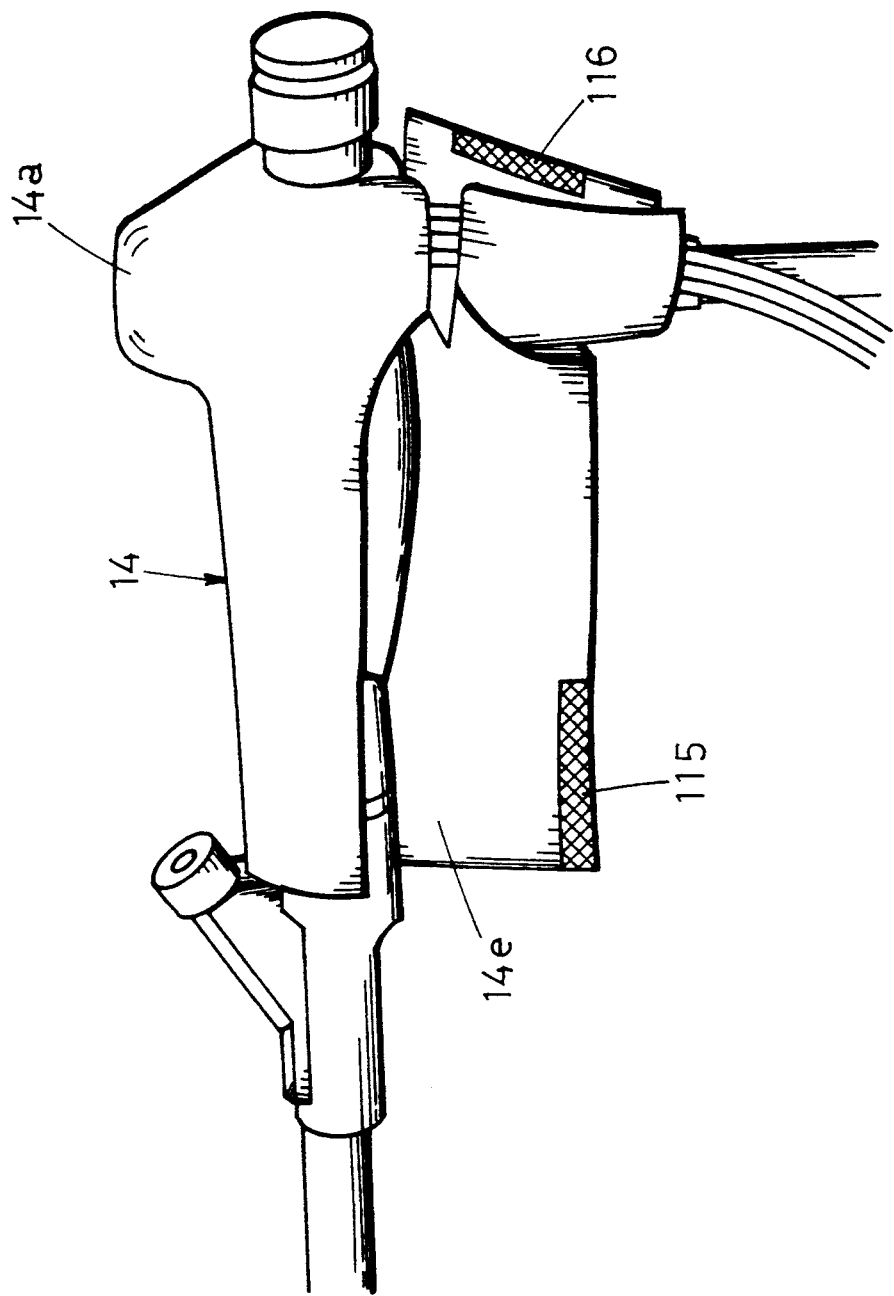
FIG. 19 is a perspective view of a control part cover in a still further embodiment of the present invention.

In any of the above-described arrangements, Velcro fasteners (so-called magic tape) 115 and 116 may be attached to the control part cover 14, as shown exemplarily in FIG. 19, so that portions of the control part cover 14 overlapping each other at the outer surface of the control part 30 are fastened together simply by pressing the control part cover 14 from the outside. The fastened portions are separated simply by pulling the control part cover 14 outwardly.

Figure 20:
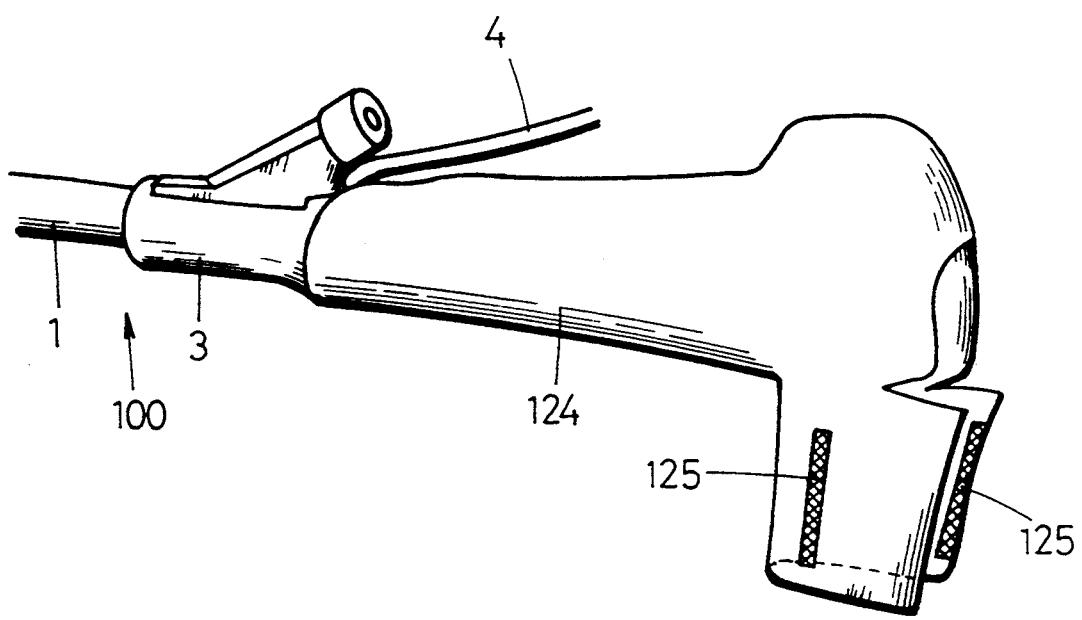
FIGS. 20 and 21 are perspective views of a control part cover in a still further embodiment of the present invention.

FIG. 20 shows a control part cover 124 in a still further embodiment of the present invention. In this embodiment, the proximal portion of the control part cover 124 is rigidly united to the mouth member 3 of the sheath 100. The fluid supply tube 4 is drawn out from the mouth member 3 to the outside of the control part cover 124.

Figure 21:
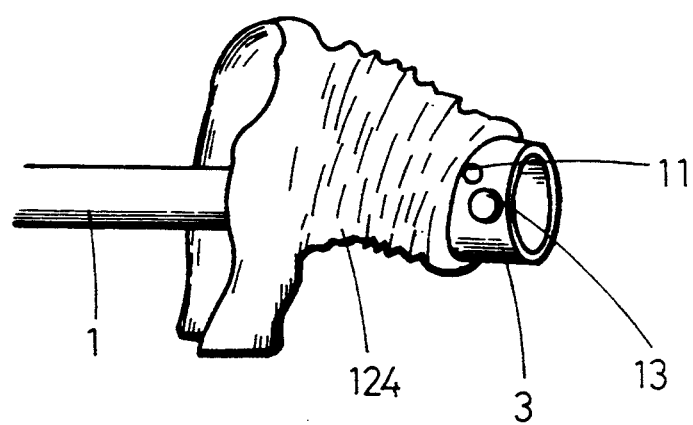

In this case, the control part cover 124 is formed in a tubular shape as a whole. When attached to and removed from the control part 30, the control part cover 124 is turned up toward the tubular member 1, as shown in FIG. 21. Reference numeral 125 denotes Velcro fasteners.

Although in the foregoing embodiments the fluid supply tubes for air supply, water supply and suction are employed, it should be noted that the present invention is not necessarily limitative thereto. It is also possible to employ only one or two of the fluid supply tubes or use tubes for supplying other fluids.

The present invention may also be applied to endoscopes wherein the control of air supply, water supply and suction is effected by actuating electric switches provided on the control part, and also to video endoscopes wherein a solid-state imaging device is employed as an image transmitting device. In addition, the present invention is applicable not only to endoscopes for medical use but also to those for industrial use.

According to the present invention, the control part cover comprises a spreadable sheet which is separate from the sheath, so that, after the completion of an endoscopy, the control part cover alone can be removed before the sheath is removed from the endoscope. It is therefore unnecessary to turn over the control part cover toward the sheath as in the prior art. In addition, the sheath can be removed without trailing the control part cover. Accordingly, it is possible to prevent contamination of the endoscope and the surroundings, when the cover device is removed from the endoscope.

In addition, when the control part cover is to be attached to the control part, the bag portion or the engagement hole formed in the control part cover is engaged with the projection of the control part, thereby enabling the control part cover to be tightly wound around the outer surface of the control part readily and reliably.

In addition, according to the present invention, the fluid supply tubes are disposed along the outside of the control part cover. Therefore, after the completion of an endoscopy, the fluid supply tubes alone can be removed before the control part cover wrapping the control part is removed therefrom. The control part cover may be removed from the control part in the end of the cover device removing operation. Accordingly, there is no possibility that contaminated hands (gloves) having touched the control part cover will touch the control part. Accordingly, contamination of the control part is prevented, and it is possible to more completely prevent the contagion of bacteria and viruses through the endoscope.

If the control part cover is secured to the control part by the fluid supply tubes, the structure is simplified and the operation of attaching and removing the control part cover is facilitated, and the likelihood of environmental contamination is further reduced.

If the fluid supply channel open-close control is effected at the control part with the control part cover sandwiched between the control part and the fluid supply tubes, the control part will not be contaminated at all no matter how the tubes are contaminated.

While the invention has been described by reference to specific embodiments chosen for purposes of illustration, it should be apparent that numerous modifications could be made thereto by those skilled in the art without departing from the basic concept and scope of the invention.

We claim:

1. A cover device which is removably fitted over an endoscope to cover an insert part of said endoscope and a control part connected to a proximal end of said insert part, said cover device comprising:

a tubular sheath for covering said insert part so as to isolate it from the outside;

a first securing means for securing said proximal end of said sheath to said proximal end of said insert part;

a control part cover for wrapping said control part, said control part cover being separate from said sheath and spreadably provided in contiguity with said proximal end of said sheath, said control part cover being a flexible sheet having opposed edges, said flexible sheet being wrapped around and secured to said control part so that said opposed edges overlap each other on a surface of said control part; and second securing means on said control part cover for securing said control part cover to said tubular sheath.

2. A cover device according to claim 1, further comprising cover securing means for securing said control part cover to said control part.

3. A cover device according to claim 2, wherein said cover securing means has a bag portion formed on said control part cover so as to be put on and engaged with a projection of said control part.

4. A cover device according to claim 3, wherein said cover securing means has a hole formed on said control part cover, so as to be engaged with said projection over said first bag portion put on said projection.

5. A cover device according to claim 3, wherein said cover securing means has a second bag portion formed on said control part cover, so as to be engaged with said projection over said first bag portion put on said projection.

6. A cover device according to claim 2, wherein said cover securing means has a detachable member for pressing said control part cover against said control part from the outside thereof, said control part cover being wound around an outer surface of said control part.

7. A cover device according to claim 1, wherein said control part cover is transparent.

8. A cover device according to claim 1, wherein said sheath is provided with an air supply opening for supplying air into said sheath to inflate it, said air supply opening being covered with said control part cover.

9. A cover device according to claim 1, wherein said control part cover is semitransparent.

10. A cover device according to claim 1, further comprising a fluid supply tube disposed such that one end portion of said tube extends through said sheath to communicate with a distal end of said sheath, and an other end portion of said tube extends from the proximal end of said sheath along an outside of said control part cover.

11. A cover device according to claim 10, further comprising tube securing means for securing said fluid supply tube to an outer surface of said control part cover, wherein said tube securing means is provided on said control part, so that said fluid supply tube is secured to said control part together with said control part cover by said tube securing means, said control part cover being located between said fluid supply tube and said control part.

12. A cover device according to claim 10, further comprising a controller for opening and closing a channel formed by said fluid supply tube, which is provided on said control part.

13. A cover device according to claim 12, wherein said fluid supply tube is crushed by said channel open-close controller when the channel of said tube is to be closed.

14. A cover device according to claim 13, wherein the operation of opening and closing the channel of said fluid supply tube by said controller is conducted with said control part cover sandwiched between said control part and said fluid supply tube.

* * * * *